United States Patent [19]

Pearson

[11] 4,432,755

[45] Feb. 21, 1984

[54] STERILE COUPLING

[75] Inventor: Stephen Pearson, Ingleside, Ill.

[73] Assignee: Baxter Travenol Laboratories, Inc., Deerfield, Ill.

[21] Appl. No.: 497,963

[22] Filed: May 25, 1983

Related U.S. Application Data

[62] Division of Ser. No. 365,943, Apr. 6, 1982.

[51] Int. Cl.³ .......................... A61M 5/00; A61J 1/00

[52] U.S. Cl. .................................... 604/56; 604/411; 604/413; 604/414; 604/416; 604/905; 141/329

[58] Field of Search .......... 604/56, 403, 408, 410–416, 604/905; 285/3, 260; 141/329, 330; 206/219, 222

[56] References Cited

U.S. PATENT DOCUMENTS

| | | | |
|---|---|---|---|
| Re. 29,656 | 6/1978 | Chittenden et al. . | |
| 2,724,383 | 11/1955 | Lockhart . | |
| 2,735,430 | 2/1956 | Huber . | |
| 2,798,488 | 7/1957 | Hall . | |
| 2,800,269 | 7/1957 | Smith . | |
| 2,904,043 | 9/1959 | Friedman . | |
| 2,955,595 | 10/1960 | Semple . | |
| 3,001,525 | 9/1961 | Hendricks . | |
| 3,033,202 | 5/1962 | Richter et al. . | |
| 3,033,203 | 5/1962 | Barton . | |
| 3,059,643 | 10/1962 | Barton . | |
| 3,110,309 | 11/1963 | Higgins . | |
| 3,123,072 | 3/1964 | Bellamy, Jr. . | |
| 3,150,661 | 9/1964 | Maki . | |
| 3,191,655 | 6/1965 | McCord . | |
| 3,214,504 | 10/1965 | Gemberling . | |
| 3,260,777 | 7/1966 | Brandt . | |
| 3,286,010 | 11/1966 | Van Groningen . | |
| 3,336,924 | 8/1967 | Sarnoff et al. . | |
| 3,369,708 | 2/1968 | Hein . | |
| 3,375,824 | 4/1968 | Krakuer et al. . | |
| 3,470,867 | 10/1969 | Goldsmith . | |
| 3,477,432 | 11/1969 | Shaw . | |
| 3,519,158 | 7/1970 | Anderson . | |
| 3,542,023 | 11/1970 | Ogle . | |
| 3,548,825 | 12/1970 | Shaw . | |
| 3,578,037 | 5/1971 | Flynn . | |
| 3,608,709 | 9/1971 | Pike . | |
| 3,659,602 | 5/1972 | Cloyd . | |
| 3,662,930 | 5/1972 | Meierhoefer . | |
| 3,776,996 | 12/1973 | Cameron et al. . | |
| 3,783,997 | 1/1974 | Brown . | |
| 3,788,369 | 1/1974 | Killinger . | |
| 3,826,260 | 7/1974 | Killinger . | |
| 3,826,261 | 7/1974 | Killinger . | |
| 3,828,779 | 8/1974 | Ogle . | |
| 3,841,329 | 10/1974 | Killinger . | |
| 3,872,867 | 3/1975 | Killinger . | |
| 3,908,654 | 9/1975 | Lhoest et al. . | |
| 3,938,520 | 2/1976 | Scislowicz et al. . | |
| 3,968,195 | 7/1976 | Bishop . | |
| 3,976,073 | 8/1976 | Quick et al. . | |
| 3,977,555 | 8/1976 | Larson . | |
| 3,995,630 | 12/1976 | van de Veerdonk . | |
| 4,019,512 | 4/1977 | Tenczar . | |
| 4,021,524 | 5/1977 | Grimsley . | |
| 4,022,205 | 5/1977 | Tenczar . | |
| 4,030,494 | 6/1977 | Tenczar . | |
| 4,102,451 | 7/1978 | Clarke et al. . | |
| 4,109,815 | 8/1978 | Collins . | |
| 4,136,775 | 1/1979 | Zaltman . | |
| 4,157,723 | 6/1979 | Granzow et al. . | |
| 4,161,178 | 7/1979 | Genese . | |
| 4,161,949 | 7/1979 | Thanawalla . | |
| 4,181,140 | 1/1980 | Bayham et al. . | |
| 4,187,846 | 2/1980 | Lolachi et al. . | |
| 4,191,225 | 3/1980 | Ogle . | |
| 4,195,632 | 4/1980 | Parker et al. . | |
| 4,197,942 | 7/1980 | Gacki et al. . | |
| 4,201,208 | 5/1980 | Cambio, Jr. . | |
| 4,223,675 | 9/1980 | Williams . | |
| 4,256,106 | 3/1981 | Shoor . | |
| 4,259,952 | 4/1981 | Avoy . | |
| 4,265,280 | 5/1981 | Ammann et al. . | |
| 4,282,863 | 8/1981 | Beigler . | |
| 4,294,247 | 10/1981 | Carter et al. . | |
| 4,325,417 | 4/1982 | Boggs et al. . | |
| 4,328,802 | 5/1982 | Curley et al. . | |
| 4,340,049 | 7/1982 | Munsch . | |
| 4,381,776 | 5/1983 | Latham | 604/408 X |
| 4,392,850 | 7/1983 | Elias et al. | 604/413 X |
| 4,392,851 | 7/1983 | Elias | 604/413 X |

FOREIGN PATENT DOCUMENTS

| | | |
|---|---|---|
| 1373027 | 8/1964 | France . |
| 2473017 | 7/1981 | France . |

WO81/01241 5/1981 PCT Int'l Appl. .
1591989 7/1981 United Kingdom .

*Primary Examiner*—Dalton L. Truluck
*Assistant Examiner*—Michelle N. Lester
*Attorney, Agent, or Firm*—Paul C. Flattery; John P. Kirby, Jr.; Bradford R. L. Price

[57] ABSTRACT

A sterile coupling enabling the selective establishment of a sterile pathway between two separate receptacles. A preferably injection molded plastic junction is made about at least the end portions of access means to each of the separate receptacles. The junction provides a sterile coupling so as to selectively bring the access means into pathway communication and thereby establish a sterile pathway between the receptacles through the access means. Also disclosed are methods for manufacturing a sterile coupling and methods for establishing a sterile pathway between the receptacles, as well as a method for low pressure injection molding.

4 Claims, 18 Drawing Figures

FIG. 1
FIG. 2
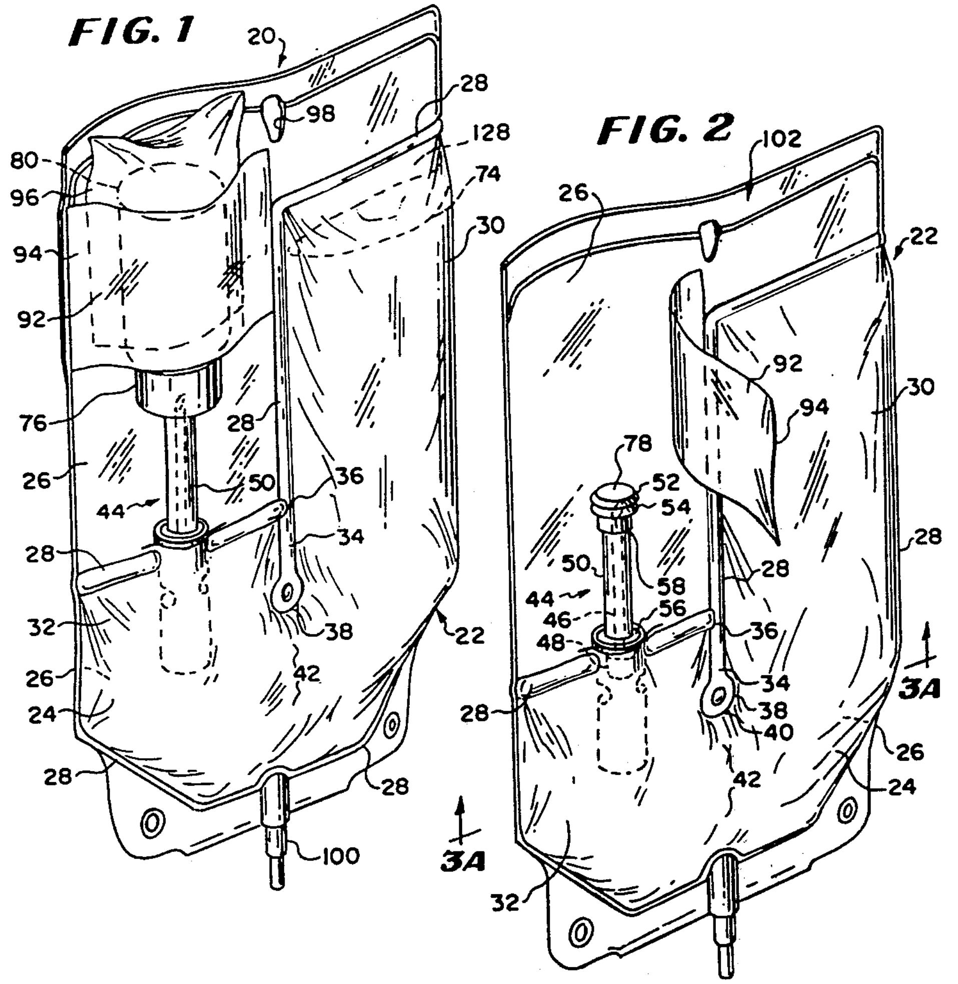
FIG. 3A
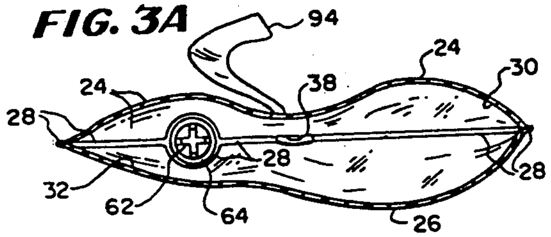

FIG. 10
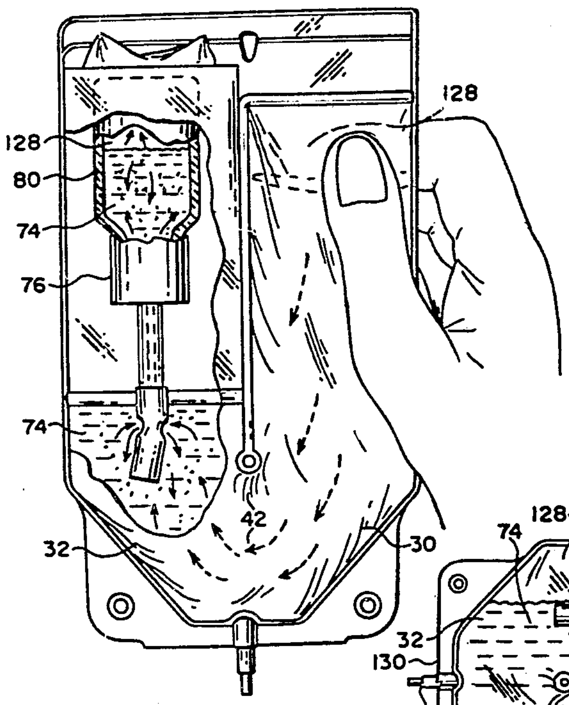
FIG. 11
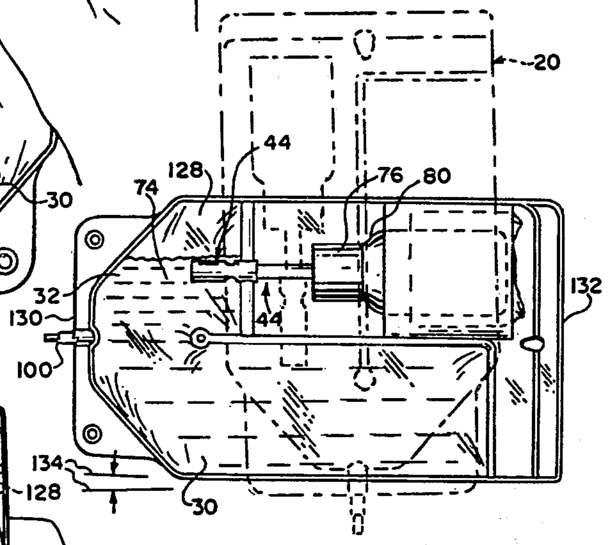
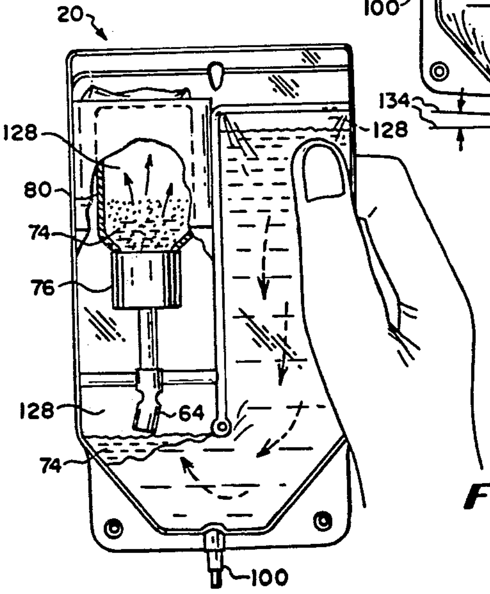
FIG. 12A

STERILE COUPLING

This is a division of application Ser. No. 365,943, filed Apr. 6, 1982.

DESCRIPTION

There are two related cases filed concurrently herewith, entitled "Closed Drug Delivery System", filed in the names of Stephen Pearson and Steffen A. Lyons, U.S. Pat. application Ser. No. 365,942; and "Mixing Apparatus", filed in the name of Steffen A. Lyons, U.S. Pat. application Ser. No. 365,945. Both applications are assigned to the assignee of the present invention.

BACKGROUND OF THE INVENTION

Many drugs are mixed with a diluent before being delivered intravenously to a patient. The diluent may be, for example, a dextrose solution, a saline solution or even water. Many such durgs are supplied in powder form and packaged in glass vials. Other drugs, such as some used in chemotherapy, are packaged in glass vials in a liquid state.

Powdered drugs may be reconstituted in a well known manner, utilizing a syringe which is used to inject liquid into the vial for mixing, the syringe eventually withdrawing the mixed solution from the vial. When a drug must be diluted before delivery to a patient the drug is often injected into a container of diluent, where the container may be connected to an administration set for delivery to a patient. More specifically, the diluent is often packaged in glass bottles, or flexible plastic containers such as are sold under the names MINI-BAG TM and VIAFLEX ® by Travenol Laboratories, Inc. of Deerfield, Illinois. These containers have administration ports for connection to an administration set which delivers the container contents from the container to the patient. The drug is typically added to the container through an injection site on the container.

Drugs may be packaged separately from the diluent for various reasons. One of the most important reasons is that some drugs do not retain their efficacy when mixed with a diluent and thus cannot be stored for any substantial period of time. In some instances the drug and diluent will not stay mixed for a significant length of time. Also, drugs are often packaged separately from the diluent because many firms which manufacture drugs are not engaged in the business of providing medical fluids in containers for intravenous delivery.

Therefore, a doctor, nurse, pharmacist or other medical personnel must mix the drug and diluent. This presents a number of problems. The reconstitution procedure is time consuming. The operator must provide the proper diluent and a syringe before beginning. Often the powdered drug is "caked" at the bottom of the vial. Thus, when liquid is injected into the vial from a syringe the surface area of contact between the liquid and the powdered drug may be quite small initially, thus making the mixing procedure even more time consuming. Because of the limited vial volume, the increasing drug concentration in the diluent makes it harder to finish the reconstitution process. The operator may attempt to solve this by repeatedly injecting solution into the vial, mixing and withdrawing the solution but this makes necessary additional injections and movement of the syringe which increase the likelihood of contamination. Also, it is sometimes difficult to get all of the drug and/or liquid out of the vial, thus increasing the time required to perform the reconstitution procedure.

The reconstitution procedure should be performed under preferably sterile conditions. In addition to such a requirement making the operator justifiably more cautious and consuming more time, sterile conditions are often hard to maintain. In some instances, a laminar flow hood may be required under which the reconstitution procedure is performed.

Some drugs such as, for example, some chemotherapy drugs, are toxic. Exposure of the operator to the drugs during reconstitution may be dangerous, especially if the operator works with such drugs on a daily basis and is repeatedly exposed to them.

A further problem is that the reconstitution procedure provides a source of confusion as to which container contains which drug, because the diluent container must be marked with the drug with which it has been injected or at least the name of the patient to whom it should be delivered.

It can be seen that a closed system for separate storage of a drug and diluent would be most beneficial. Certain factors have until recently prohibited such a closed system on a commercially feasible, reasonably inexpensive bases, however. One factor which has made difficult the manufacture of a closed system having separate, selectively communicating compartments for a drug and a diluent has been the sterilization procedure. As an example, in the case of diluent in a flexible plastic container, the container with the diluent therein is sterilized by steam sterilization, or autoclaving. However, the heat generated during such a sterilization procedure would destroy the efficacy of many drugs. On the other hand, other sterilization means such as the use of ethylene oxide gas may not harm the drug but may harm the diluent. A system for sterilizing a drug and diluent separately and combining the two components into a single, container having separate compartments for separate storage after sterilization is shown in a U.S. Pat. application in the name of William Schnell, entitled "Sterilized Liquid Mixing System" U.S. Pat. application Ser. No. 365,940, filed concurrently herewith and assigned to the assignee of the present invention.

These considerations mandate that, absent means to protect the drug and diluent during different sterilization steps, the system be formed by combining separate drug and diluent receptacles after they have been separately sterilized. This requires the manufacture of a sterile or at least an aseptic connection between the two receptacles. Sterile connectors are known, such as shown, for example, in U.S. Pat. Nos. 4,157,723 and 4,265,280 and allowed U.S. Pat. application Ser. No. 027,575, filed on Apr. 6, 1979, now U.S. Pat. No. 4,325,417 all assigned to the assignee of the present invention. The connectors disclosed therein provide highly reliable, sterile connections. They do however employ a separate radiant energy source to make the connection and therefore a power supply to operate the energy source.

Another requirement of such a closed system is that it should prevent water vapor transmission from the receptacle holding the diluent to the receptacle holding the powdered drug. As discussed earlier, the storage of some powdered drugs with even a small amount of liquid destroys drug efficacy.

Finally, such a closed system should also be constructed in a manner which will facilitate easy and thorough mixing of the drug and the diluent.

SUMMARY OF THE INVENTION

The present invention is directed to a sterile coupling which enables the selective establishment of a sterile pathway between two separate receptacles. The sterile coupling of the present invention can be made directly to a drug vial of standard construction without modification of the drug vial. The sterile coupling enables separate sterilization of two components in separate receptacles yet makes possible a closed system for storage of the components in a manner enabling their future combination under sterile conditions.

Each of the receptacles includes access means. A molded junction is permanently affixed about at least the end portions of both of the access means to maintain the end portions in sterile, spaced relation. One of the access means includes a piercing element capable of piercing the junction between the end portions, thereby establishing a sterile pathway between the receptacles through the access means. In the preferred embodiment, the molded junction is a plastic material which is formed by injection molding the heated molten plastic about the end portions. The junction provides for sterilized end portions to later form a sterile coupling by means of heat transfer from the molten material to the end portions.

The present invention is further directed to a method for establishing and maintaining a sterile, spaced relation between the access means of each of two separate receptacles, allowing for the future selective establishment of a sterile pathway between the receptacles through the access means.

The invention further provides a method for selectively establishing a sterile pathway between access means of each of two separate receptacles.

Finally, the invention is also directed to a method for injection molding molten material from a low pressure supply into a mold interior. Low pressure injection molding is necessary when, for example, it is desired to injection mold a junction about an easily damaged glass vial.

DESCRIPTION OF THE DRAWINGS

FIG. 1 is a perspective view of the closed system.

FIG. 2 is a perspective view of the compressible chamber seen in FIG. 1.

FIG. 3A is a fragmentary view taken along the line 3A—3A of FIG. 2.

FIG. 10 is a partially cut-away, front elevational view illustrating liquid exchange.

FIGS. 11, 12A and 12B are front elevational views of the container illustrating the step of emptying the liquid from the container into the chamber.

DETAILED DESCRIPTION OF THE PREFERRED EMBODIMENTS

Figure 3B:
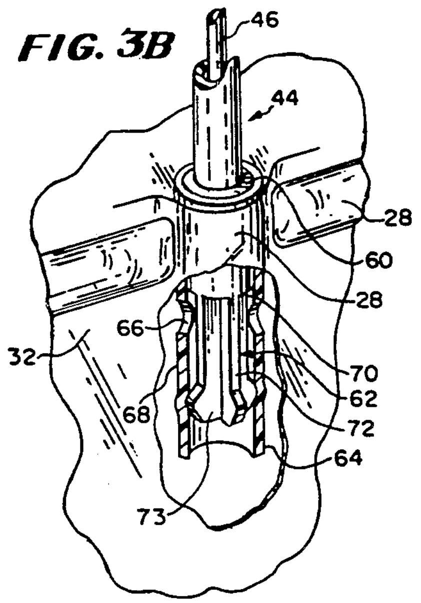
FIG. 3B is an enlarged fragmentary view in partial cross-section of the retaining tube and frangible cannula.

Referring to FIGS. 1 through 3, there is seen in FIG. 1 a closed system 20. A compressible chamber 22 is provided which may be made from flexible plastic sheets 24, 26 sealed together to form an external seal 28 about the compressible chamber 22. The plastic sheets 24, 26 may be made of, for example, polyvinyl chloride material and the external seal 28 may be, for example, a heat seal or a radio-frequency (RF) seal. The compressible chamber 22 includes a reservoir compartment 30 and a selectively gas-trapping compartment 32. The reservoir and gas-trapping compartments 30, 32 are partially defined by an internal wall 34 having a closed end 36 and an open end 38. The internal wall 34 may also be formed by heat sealing or RF sealing the two flexible plastic sheets together. The internal wall 34 may be an extension of the external seal 28. The open end 38 of the internal wall 34 may be a wider, rounded seal 40 for increased strength.

The internal wall 34 segregates the gas-trapping and reservoir compartments 32, 30 along the length of the internal wall 34 and at the closed end 36. The internal wall 34 defines an open flow path 42 around the open end 38, between the gas-trapping and reservoir compartments 32, 30.

The external seal 28 and internal wall 34 together define a generally "J"-shaped configuration for the compressible chamber 22 in the preferred embodiment. The reservoir compartment 30 corresponds to the long leg of the J-shaped configuration and the gas-trapping compartment 32 corresponds to the short leg of the J-shaped configuration. The internal wall 34 separates the long and short legs.

Means 44 to access the compressible chamber 22 is located adjacent the gas-trapping compartment 32. In the preferred embodiment the access means includes a needle 46 which may be of standard construction, mounted in a plastic needle hub 48. The chamber access means 44 further includes a plastic, flexible sleeve 50 such as may be made with polyvinyl chloride material. The sleeve 50 may be bonded at its first end 56 to the needle hub 48, by conventional means such as solvent bonding. The chamber access means 44 further includes a membrane 52 bonded to and closing the sleeve 50 at the second end 58 of the sleeve. The membrane 52 includes annular ribs 54. The membrane 52 may also be a plastic material.

The first end 56 of the sleeve 50 is secured into the hollow end 60 of a frangible cannula 62. Such frangible cannulas are known and may be constructed as shown for example, in U.S. Pat. Nos. 4,181,140 and 4,294,247 and allowed U.S. Pat. application Ser. No. 086,102 filed Oct. 18, 1979, now U.S. Pat. No. 4,340,049 all assigned to the assignee of the present invention. Referring to FIGS. 3A and 3B, it is seen that the frangible cannula 62 may be housed in a hollow retaining member 64 which includes one or more openings 66 in the sidewall 68 of the retaining member 64, the openings 66 being located near the top of the short leg of the J-shaped compressible chamber 22. The frangible cannula 62 includes a breakaway portion 72 which may have fins 73 and which may be selectively broken away from the hollow end 60 at the frangible portion 70.

As seen best in FIGS. 1 and 3B, the external seal 28 is made around the sidewall 68 of the retaining member 64. If RF sealing is utilized, the sidewall 68 of the retaining member 64 will simultaneously seal to the plastic sheets 24, 26 and to the hollow end 60 of the frangible cannula 62 upon application of the RF source.

The compressible chamber 22 contains a first component 74 which may be a sterile liquid diluent such as water, dextrose solution or saline solution. Other diluents are of course possible.

The closed system 20 preferably includes hanging means such as a defined opening 98 through the flexible plastic sheets 24, 26. The compressible chamber 22 preferably includes a selectively opened port 100 which may be connected to an administration set (not shown) for delivery to the venous system of a patient.

Figure 6:
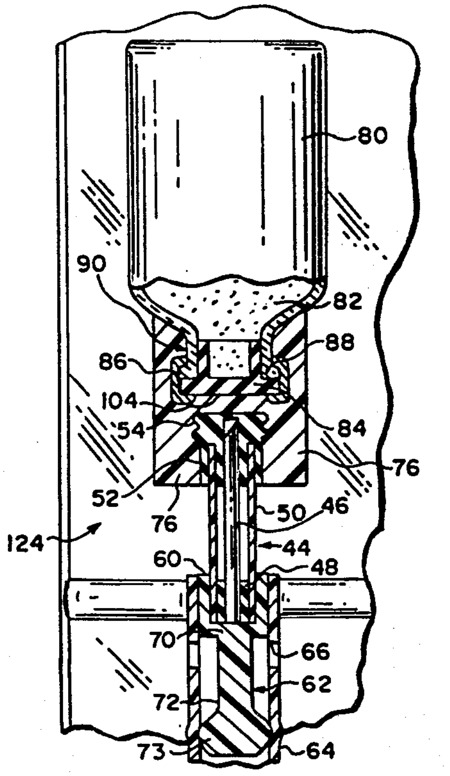
FIG. 6 is a fragmentary, cross-sectional view of the sterile coupling used in the closed system illustrated in FIG. 1.

Referring to FIGS. 1 and 6, a junction 76 encloses the end portion 78 of the chamber access means 44. In the preferred embodiment the junction 76 is made from an injection moldable plastic material. The junction 76 connects the chamber access means 44 with a container 80. The container 80 contains a second component 82 such as a powdered or liquid drug. In the preferred embodiment, the container 80 is a glass drug vial of standard construction, which allows for the incorporation of drugs into the closed system 20 from other sources in such standard vials without necessitating retooling for a new drug container. When the container 80 is a drug vial of such standard construction, it typically includes a rubber stopper 84 and a metal band 86 about the mouth 88 of the container 80, the metal band 86 retaining the rubber stopper 84 in the container 80. The rubber stopper 84 and metal band 86 together form means 90 to access the container 80. As will be described below, neither the chamber access means 44 nor the container access means 90 are limited to the specific construction described herein, but rather can include a wide range of configurations.

The container 80 may be loosely retained by a flap 92 extending from the flexible plastic sheet 24 and heat sealed at its distal end 94 to the other flexible plastic sheet 26. A plastic pouch 96 is placed about the container 80. The plastic pouch 96 may be of a polyolefin material against which the container 80 may easily slide. The polyolefin material has a lower coefficient of friction than, for example, polyvinyl chloride, from which the flexible plastic sheets 24, 26 may be made.

Figure 4:
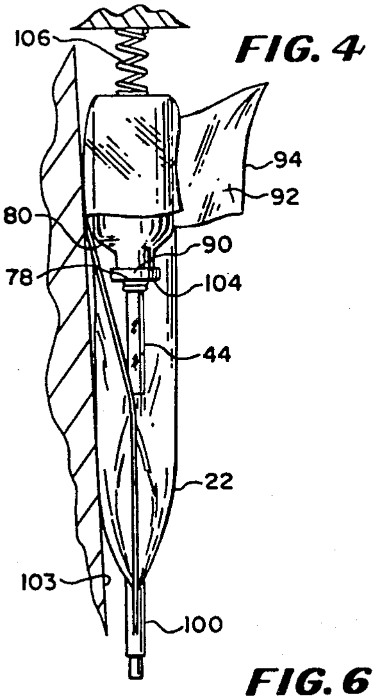
FIG. 4 is a partially schematic side elevational view of the closed system during manufacture rotated ninety degrees for ease of illustration on the page.

The closed system 20 is manufactured by bringing together the compressible chamber 22 and the container 80 after the contents of each has been separately sterilized. For example, after the apparatus 102 seen in FIG. 2 is filled with the first component 74 it may be placed in a closed pouch (not shown) of a plastic material such as polypropylene. The apparatus 102 may then be subjected to autoclaving to sterilize the interior of the compressible chamber 22 and the first component 74. The apparatus 102 is then taken out of the pouch and placed on a preferably horizontal surface 103 at a work station with the flexible plastic sheet 24 and the flap 92 face up, as illustrated in FIG. 4. Fig. 4 has been rotated ninety degrees for ease of illustration on the page. The pouching of the apparatus 102 before autoclaving is helpful in promoting a clean environment for the apparatus but is not necessary. For example, the apparatus 102 may be autoclaved without pouching. After this step, the apparatus can be taken directly to the work station.

The flap 92 is folded away from the chamber access means 44. The container 80 is then placed on the horizontal surface 103. The end portion 104 of the container access means 90 is biased into abutting relation with the end portion 78 of the chamber access means 44. The end portions 78, 104 may be biased by any appropriate biasing means, such as, for example, a spring mechanism 106.

Figure 5:
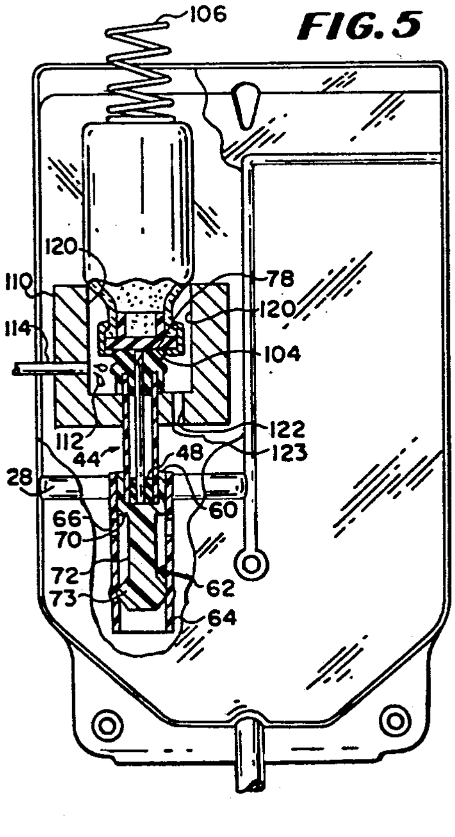
FIG. 5 is a front elevational view in partial cross-section of the system illustrated in FIG. 1, during manufacture.

As seen in FIG. 5, a mold 110 is then placed about the end portions 78, 104 of the chamber access means 44 and container access means 90, respectively. Molten material 112 is then injected through the supply line 114 into the mold interior 120, about the end portions 78, 104. It is anticipated that the molten material 112 will be a plastic, and preferably a thermoplastic; however, it is conceivable that other molten materials meeting the requirements described below will also work. In the preferred embodiment, the molten material is a plastic sold under the trademark Kraton by Shell Oil Company. It is believed that Kraton is block copolymer of polystyrene and a rubbery polyolefin material. Another plastic which may be acceptable is Delrin ®, sold by E. I. DuPont de Nemours & Co. The plastic should be puncturable but resistant to coring during puncture. The pressure of the injected molten material 112 overcomes the bias between the end portions 78, 104 and separates the end portions into spaced relation as seen in FIG. 6.

In order to be in a molten state, the molten material such as molten plastic will be quite hot. It has been found that during injection molding the molten material sterilizes the end portions 78, 104 of both access means 44, 90 by heat transfer from the injection molded molten material 112. When Kraton is used, a temperature of 500° F. or more should be maintained so as to sterilize the end portions 78, 104. Generally, a higher temperature for the molten material 112 will improve the sterilizing ability of the heat transfer during injection molding.

It has been found that spraying water on the end portions 78, 104 before injection of the heated molten material 112 may improve the sterilizing ability of the heat transfer, although this is not believed necessary in the preferred embodiment.

The molten material 112 is then cooled into a unitary junction 76 which encloses the end portions 78, 104 and also maintains the end portions in sterile, spaced relation, as seen in FIG. 6. In addition to establishing and maintaining a sterile spaced relation between the access means 44, 90 the above-described method provides an arrangement whereby a piercing element such as, for example, the needle 46 may be urged through the junction 76 to selectively establish a sterile pathway 118 between the compressible chamber 22 and container 80 through both access means 44, 90, as seen for example, in FIGS. 7 and 8.

It is believed that the above-described method for establishing and maintaining the sterile spaced relation between the access means may be accomplished without biasing the end portions 78, 104. Alternatively, the end portions may be held or maintained in a predetermined spaced relation. The molten material may then be injected about at least the end portions 78, 104 of both access means 44, 90. In this alternative method, the injection molding of the molten material does not itself separate the end portions 78, 104, but the step does sterilize the end portions.

It is believed that since, in the preferred embodiment, the injection molding of molten material occurs only about the container access means 90 of the container 80, only a minimum amount of heat transfer occurs between the molten material 112 and the second component 82 such as a powdered drug in the container 80, thus maintaining the efficacy of the drug. When a glass vial is used as the container 80, the glass serves as a good insulator against heat transfer between the molten material 112 and the second component 82 inside the vial. The rubber stopper 84 also is a good insulator.

It may be seen that the above-described method for establishing and maintaining a sterile spaced relation between the access means 44, 90 is not limited to access means of the specifically described chamber 22 and container 80. Indeed, any two receptacles may be used in place of the chamber 22 and the container 80.

As stated, the container 80 in the preferred embodiment is a glass vial having a rubber stopper 84 in the mouth 88 of the vial. Because of the use of a glass construction and a rubber stopper 84, the container 80 can not be subjected to strong stresses. For this reason, the injection molding step described above to form the junction 76 must be made from a low pressure supply into the mold interior 120. The molten material 112 is injected at a pressure of less than 10 PSI and preferably a pressure of about 5 PSI. This low pressure injection molding makes impossible an otherwise useful, known technique for determining when the mold interior 120 is full. For example, completion of an injection cycle is often determined by monitoring the back pressure in the supply line. When the back pressure of the molten material rises to a certain level it is known that the mold interior is full and injection of further plastic is then stopped. Under the low injection molding pressure requirements, however, it is difficult to determine a significant rise in back pressure of the molten material 112. If the back pressure is allowed to rise, the pressure might either blow the rubber stopper 84 into the container 80 or break the container 80.

Other means of detemining injection cycle completion include measuring the quantity of molten material injected into the mold interior through the supply line. Such measurement means can be expensive and it is often difficult to perform precise measuring.

Solving the problem of determining completion of an injection cycle is solved by providing an open channel 122 in the mold 110, as seen in FIG. 5. Preferably, the open channel 122 is a formed groove in the side of one of two mold halves which comprise the mold 110. The open channel 122 extends between the mold interior 120 and the exterior of the mold 110. The open channel 122 is preferably placed away from the supply line 114, although it is believed that this is not necessary. The open channel is relatively narrow compared with the mold interior 120 and in the preferred embodiment is within the range of about 0.030 in. to about 0.060 in. wide, when the molten material is Kraton. After molten material 112 has filled the mold interior 120, it enters the open channel 122. The presence of the molten material 112 in the open channel 122 is then sensed, whereupon the low pressure supply of the molten material ceases.

It is believed that by placing the mold-interior end of the open channel 122 away rom the supply line 114 and most importantly be making the open channel 122 narrow, the open channel 122 becomes the path of greatest resistance to the molten material 112 and is therefore filled with molten material 112 only after the mold interior 120 is filled. The object is to make the open channel 122 the path of greatest resistance but to prevent clogging of the channel and allow molten material to enter the channel 122. Thus, when the molten material is more viscous, the channel 122 will need to be wider so as to permit material 112 to enter the open channel and to prevent clogging of the channel 122, yet still narrow enough to be the path of greatest resistance to the molten material 112.

If the injection molding process is performed manually, the presence of the molten material in the channel 122 may be sensed visually, whereupon the operator ceases the application of pressure to the material supply. In an automated procedure, the sensing of the molten material in the channel 122 could be made by various means including, for example, a microswitch (not shown) connected to the inside of the open channel 122 or at the exterior end 123 of the open channel 122. The microswitch can be connected to and control the low pressure supply.

When the molten material 112 cools and becomes the junction 76, a sterile coupling 124 is formed which enables the selective establishment of the sterile pathway 118 between two separate receptacles, such as the container 80 and the compressible chamber 22. In the closed system 20 the sterile coupling 124 includes the chamber access means 44, the container access means 90 and the molded junction 76 affixed about at least the end portions 78, 104 of the access means 44, 90, respectively, whereby the junction maintains the end portions in sterile spaced relation. The sterile coupling 124 further includes the piercing element such as the needle 46 which is capable of piercing the junction 76 between the end portion 78, 104 so as to selectively bring the access means into pathway communication and establish a sterile pathway 118 between the container 80 and the compressible chamber 22 through the access means 44, 90. In the preferred embodiment, the needle is housed within and is a part of the chamber access means 44. The needle 46 forms the conduit between the container 80 and the chamber 22 when the sterile pathway 118 is formed. However, it is not necessary for the piercing element to be a needle 46 and it is not necessary for the piercing element to also be the conduit. Other piercing element and conduit configurations may be used in the sterile coupling 124. Indeed, the sterile coupling 124 is not limited to use in the above-described closed system 20. For example, the sterile coupling 124 can include first means to access one receptacle and second means to access another receptacle, whereby the junction 76 is permanently affixed about at least the end portions of both the first and second access means. The piercing element should be capable of piercing the preferably plastic junction from the end portion of the corresponding access means through the junction at least to the end portion of the other of the first and second access means in a manner to establish a sterile pathway through both access means, between the receptacles.

Upon formation of the sterile coupling 124 in the closed system 20, the loose fitting, open ended plastic pouch 96 is placed about the container 80, as seen for example in FIG. 1. The flap 92 is then brought down over the container 80 and heat sealed at its distal end 94 to the flexible plastic sheet 26. The plastic sheet 26, flap 92 and pouch 96 confine the container 80 but allow for axial movement of the container. As stated above, the plastic sheet 26 and flap 94 may be made of polyvinyl chloride material. Such material has a very high coefficient of friction thereby hindering axial movement of the container 80 relative to the compressible chamber 22. The plastic pouch 96 is provided merely to reduce the coefficient of friction and ease axial movement of the container. The plastic pouch 96 may be a polyolefin such as polypropylene, for example.

Figure 7:
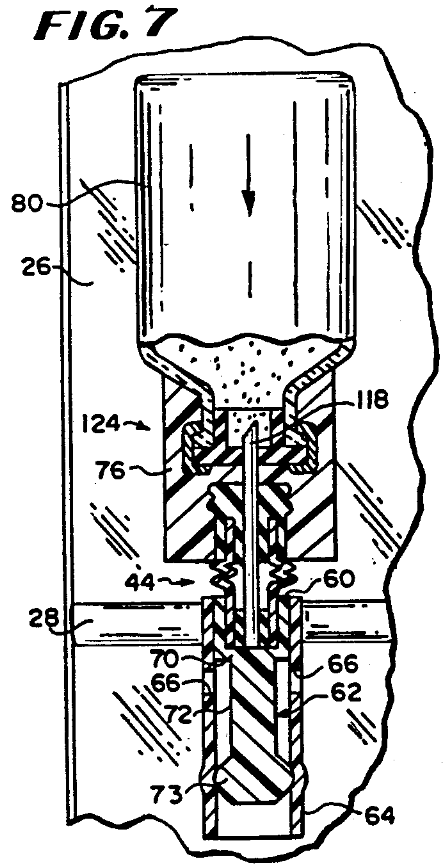
FIG. 7 is a fragmentary view of the closed system in partial cross-section, illustrating the establishment of a sterile pathway.
Figure 8:
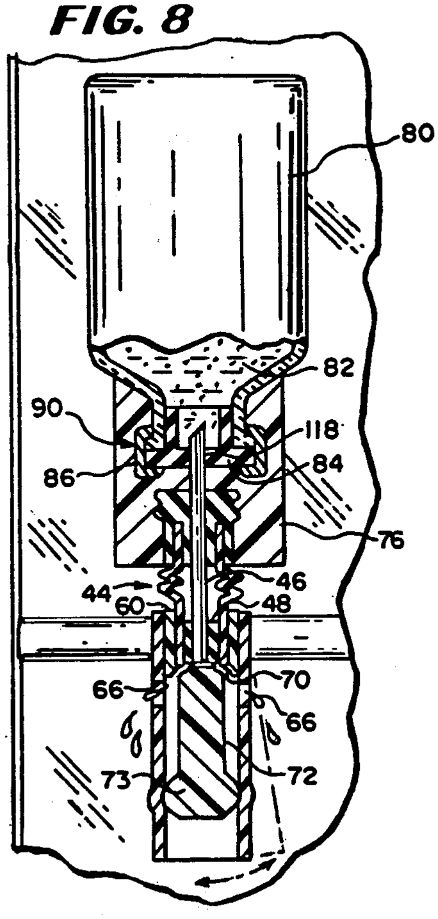
FIG. 8 is the view illustrated in FIG. 7 and further illustrating the open frangible cannula.

The closed system 20 provides for the separate storage of two components and the selective mixing of those components under sterile conditions. The first component 74 in the compressible chamber 22 and the second component 82 in the container 80 are mixed by first forming the sterile pathway 118 within the junction 76 of the sterile coupling 124, as illustrated in FIGS. 7 and 8. In the preferred embodiment the sterile pathway 118 is made by urging the percing element, in this case the needle 46, through the membrane 52 and the end portion 78 of the chamber access means 44. After piercing the membrane 52, the needle 46 pierces the junction 76 and then the rubber stopper 84 of the container 80, the rubber stopper 84 being part of the container access means 90. The interior of the needle 46 is then in communication wih the interior of the container 80 housing the second component 82. The piercing element is urged toward the container 80 by simply grasping the container 80 and the chamber access means 44 and pushing them toward each other. The closed system 20 allows for axial movement of the container 80.

When the container 80 and needle 46 are urged together as seen in FIG. 7, the sleeve 50 collapses because of its flexible construction. The sleeve 50 and membrane 52 serve to hold the chamber access means 44 within the junction. The annular ribs 54 about the membrane 52 aid in retaining the membrane 52 within the junction 76. If the junction 76 were molded directly about the needle 46 it might be possible to withdraw the needle 46 from the junction 76. While it is believed that such a configuration of the invention will work, the chamber access means 44 including the sleeve 50 and membrane 52, is preferred.

The frangible cannula 62 segregates the liquid first component 74 from the chamber access means 44, preventing the collection of liquid within the sleeve 50 before the frangible cannula 62 is opened. In addition, the frangible cannula 62 provides further assurance that there will be no contamination of the first component 74 stored in the compressible chamber 22. To completely open the sterile pathway 118 between the interiors of the chamber 22 and container 80, the frangible cannula 62 must be opened. This is done by manipulating the cannula 62 from exterior of the compressible chamber 22. The break-away portion 72 is bent relative to the hollow end 60, fracturing the cannula 62 at frangible portion 70. If desired, the break-away portion 72 may thereafter be urged away from the hollow end 60 down the retaining member 64. The frangible cannula 62 may be designed so as to include fins 73 on the break-away portion 72 which frictionally engage the retaining member 64. The break-away portion 72 is thus trapped in the retaining member 64 and does not float loosely within the chamber 22.

After the sterile pathway 118 is formed and after the frangible cannula 62 is opened, fluid flow between the container 80 and chamber 22 is made through the needle 46 and around the fins 73 of the frangible cannula 62 as well as through the defined opening 66 in the retaining member 64. Once the sterile pathway 118 is established, the gas-trapping and reservoir compartments 32, 30, respectively, may be selectively positioned to facilitate the proper mixing of the first and second components 74, 82.

The mixing procedure is best seen with reference to FIGS. 9 through 12. The method includes the steps of transferring some of the liquid first component 74 into the container 80 after at least some air 128 is in the container 80, exchanging some of the liquid in the container with some of the liquid in the chamber 22 and finally, emptying the liquid in the container 80 into the chamber 22.

In the illustrated embodiment the liquid, first component 74 is stored in the compressible chamber 22 along with at least a small amount of air 128 or other gas. The first component 74 may be packaged without any air 128 in the compressible chamber if there is some air 128 stored in the container 80. Powdered drugs are often stored in drug vials under partial vacuums, however, and thus additional air is required for the working of the invention. Thus, air 128 is stored in the chamber 22.

Figure 9:
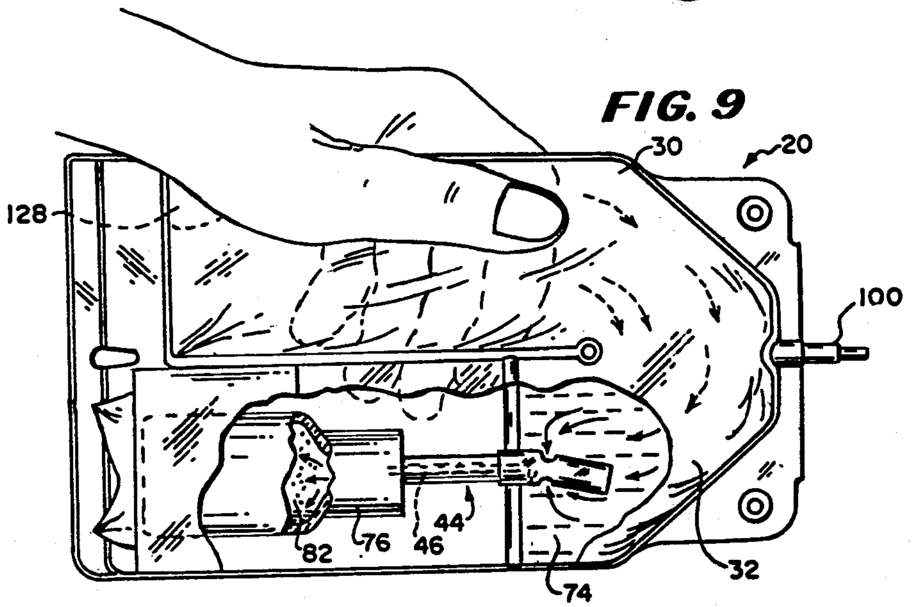
FIG. 9 is a partially cut-away, front elevational view illustrating liquid transfer.

Liquid transfer from the chamber 22 into the container 80 is accomplished by manipulating the chamber 22 until the liquid first mixing component 74 is adjacent the chamber access means 44, as seen in FIG. 9. The chamber 22, being made of flexible plastic sheets 24, 26, may be manually compressed, thereby urging some liquid from the chamber 22 into contact with the second mixing component 82 in the container 80. The liquid is transferred most easily if the closed system 20 is maintained horizontally with the gas-trapping compartment 32 and the container 80 beneath the reservoir compartment 30, such as is shown in FIG. 9. It is important to stop compression of the chamber 22 before the container 80 is totally filled with liquid. If the container 80 is packaged with a vacuum, it would otherwise be possible to fill the container totally with liquid.

After some of the first component 74 is in the container 80, the container 80 is agitated by shaking the closed system 20. This mixes the first component 74 with the second component 82. In those instances where the second component 82 is a powder, agitation of the container is most useful in initiating a mixing between the components. This is especially true where the powder has "caked38 into a single piece, which provides for only small surface area contact between the components. Agitation helps to break up the second component 82 into smaller particles.

After the step of liquid transfer, some of the liquid in the container 80 is exchanged with some of the liquid in the chamber 22, as best seen in FIG. 10. First, the chamber is manipulated until liquid, as opposed to air 128, is in the gas-trapping compartment 32 of the chamber 22 adjacent the chamber access means 44 and until the chamber access means 44 is above the gas-trapping compartment 32. The J-shaped configuration of the compressible chamber 22 allows for liquid in the chamber 22 to be adjacent the chamber access means 44 while still holding the closed system 20 in the upright position shown in FIG. 10. Any air 128 in the chamber 22 can be stored entirely in the reservoir compartment 30. This is accomplished by manipulating the position of the closed system 20 so that air 128 in the gas-trapping compartment 32 flows through the open flow path 42.

The chamber may then be manually compressed, which urges some of the liquid in the gas-trapping compartment 32 of the chamber 22 into the container 80. During the compression step, air in the container 80 which is above the liquid in the container 80 is pressurized. Compression of the chamber is then stopped. When compression ceases the pressurized air in the container forces some of the liquid from the container into the chamber 22. The liquid first component 74 now has some of the second component 82 mixed therewith.

Were it not for the unique shape of the compressible chamber 22, the liquid exchange step would be performed by first turning the system 20 upside down so that the chamber access means 44 would be below the gas-trapping compartment and then pressing chamber. Then, while still exerting pressure on the chamber to compress it, the closed system would have to be rotated approximately 180° until the air in the container 80 is positioned above the liquid in the container. Only then could compression of the chamber 22 be stopped, which would then urge liquid from the container 80 into the chamber 22.

The liquid exchange step of the mixing method transfers some of the second component 82 into the chamber 22 and places additional amounts of the liquid first component 74, having a lower concentration of the second component 82 therein, into contact with any amount of second component remaining in the container 80. By placing the less highly concentrated mixture into contact with the remaining portion of the second component 82, thorough mixture of the two components 74, 82 is facilitated. The liquid exchange step may be repeated several times if necessary, or if desired to ensure thorough mixing. After each liquid exchange step is completed, the closed system 20 may be agitated to facilitate mixing. Repetition of the liquid exchange step is most useful when the second component is, for example, a powdered drug.

Figure 12B:
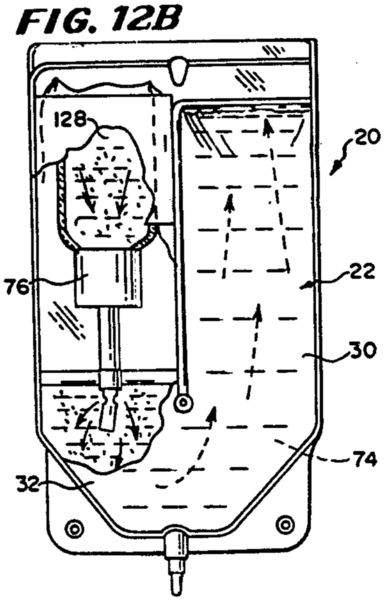

After a homogenous mixture between the first and second components has been created, or after all powder has been disolved, the liquid in the container is emptied into the chamber, leaving virtually none of either the first or second components 74, 82 in the container 80. The liquid emptying step is best illustrated in FIGS. 11, 12A and 12B. First, the chamber 22 is manipulated until at least some of the air 128 in the reservoir compartment 30 enters the gas-trapping compartment 32 through the open flow path 42 between the gas-trapping and reservoir compartments 32, 30. This is done by rotating the closed system 20 approximately 90° from the position of FIG. 10, shown by phantom line in FIG. 11, to the substantially horizontal position illustrated by solid line in FIG. 11. In order to insure that air 128 flows around the internal wall 34, through the open flow path 42 and into the gas-trapping compartment 32, it is desirable to rotate the closed system 20 until the port tube end 130 is somewhat higher than the hanging end 132. This is depicted schematically by the lines 134 in FIG. 11.

Next, the chamber is manipulated until the air 128 in the gas-trapping compartment 32 is adjacent the chamber access means 44. This arrangement is shown in FIG. 12A, in which the closed system 20 has been rotated approximately 90° counterclockwise. The internal wall 34, in addition to defining and partially segregating the gas-trapping and reservoir compartments 32, 30, also enables this above-described selective entrapment of at least a portion of the air 128 in the gas-trapping compartment 32 adjacent the chamber access means 44. The next step in emptying the liquid from the container is to compress the chamber as seen in FIG. 12A. This compression urges at least some of the air in the gas-trapping compartment 32 into the container 80, thereby pressurizing the air 128 above the liquid in the container 80. Compression of the chamber is then stopped and, as illustrated in FIG. 12B the now pressurized air in the container 80 expels the liquid in the container through the sterile pathway 118 into the chamber 22.

Mixing is now complete. A homogenous mixture is in the compressible chamber 22. The container 80 is virtually empty. The closed system 20 may now be used as a supply container to deliver the mixture in the chamber 22 directly to a patient. A spike of an administration set may be inserted into the port 100 to accomplish this fluid delivery.

The uniquely designed compressible chamber 22 of the invention may also be utilized without the sterile coupling 124 previously described. The compressible chamber having a selectively gas-trapping compartment and a reservoir compartment with an open flow therebetween, may, in combination with, or for future attachment to a container, comprise an apparatus for separately storing and selectively mixing components or for mixing a liquid first component stored therein with a second component stored in the future connected container. When the apparatus includes the compressible chamber and the container, the closed system 20 is such an apparatus, but the container and chamber may be connected by any selectively opened pathway between the chamber and container and is not limited to use of the junction 76. For example, the container 80 and chamber 22 may have a selectively opened pathway which is a conduit having a frangible cannula therein. The selectively opened pathway may have a configuration different from those described above. At least one of the container and the compressible chamber also contains a gas. The apparatus is useful for mixing two components even when sterile conditions are not necessitated.

When the apparatus does not include the container, the apparatus 102 may be as shown in FIG. 2, for example. The apparatus 102 includes means to access the gas-trapping compartment so that this access means 44 can be selectively connected to a separate container to form a selectively opened pathway between the container and chamber.

Figure 14:
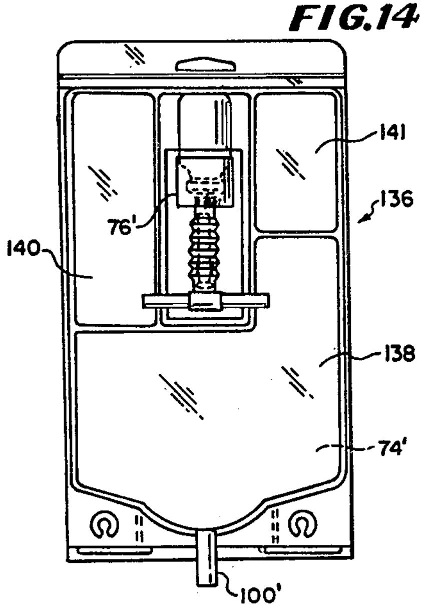
FIG. 14 is a front elevational view of another alternate embodiment of the sterile coupling.
Figure 15:
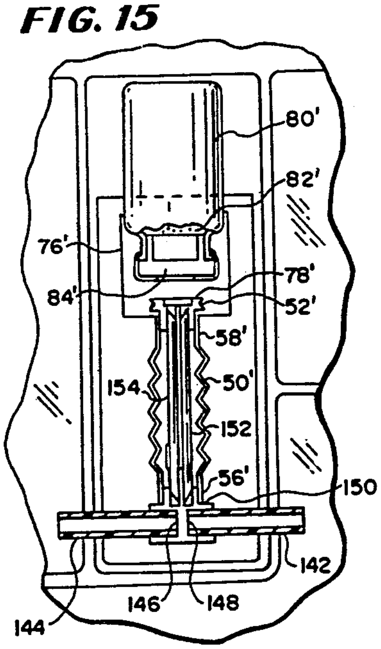
FIGS. 15 and 16 are fragmentary views in partial cross-section of the sterile coupling of FIG. 14, before and after establishment of a sterile pathway, respectively.
Figure 16:
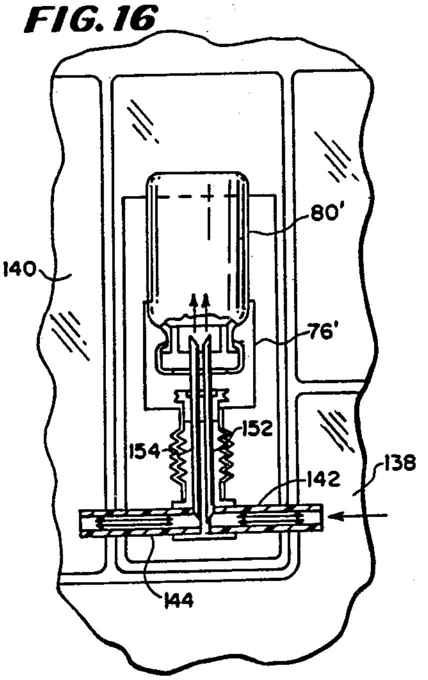

FIGS. 14 through 16 illustrate an alternate embodiment of the sterile coupling described above. In this embodiment, there is provided a closed device 136 including a compressible primary chamber 138 and a compressible auxiliary chamber 140. The chambers 138, 140 may be made from flexible plastic sheets of, for example, polyvinyl chloride. Area 141 has no function other than to provide a uniform appearance to the device 136. A port 100' provides for selective communication between the primary chamber 138 and the exterior of the device 136.

Tubes 142, 144 extend from and communicate with the interiors of primary and auxiliary chambers 138, 140, respectively. Distal ends 146, 148 of the tubes 144, 142, respectively, are closed by a cap portion 150 which may be made of a needle pierceable plastic or rubber material. The first end 56′ of a flexible sleeve 50′ is attached to the cap portion 150. The second end 58′ of the sleeve 50′ is attached to and closed by a pierceable membrane 52′. Housed within the sleeve 50′ are two double pointed needles 152, 154. Together, tubes 142, 144, cap portion 150, sleeve 50′, membrane 52′ and double pointed needles 152, 154 form first means to access a receptacle, the receptacle in this instance including both primary and auxiliary chambers 138, 140. A junction 76′ such as described above is affixed about the end portion 78′ of the first access means, which includes the membrane 52′, the sleeve 50′, the cap portion 150, the needles 152, 154 and the tubes 142, 144. The junction 76′ is also affixed about the rubber stopper 84′ of a container 80′. In this embodiment, the rubber stopper 84′ is part of the second access means to access a second receptacle, in this case the container 80′.

A liquid first component 74′ is stored in the primary chamber 138. A second compartment 82′ is stored in the container 80′. The auxiliary chamber 140 remains empty until mixing is desired, at which time the container 80′ is urged toward the first access means. Both of the double pointed needles 152, 154 puncture the junction 76′, the stopper 84′ and the cap portion 150. An open fluid passage is then established as seen in FIG. 16. The fluid passage extends from the primary chamber 138 through the tube 142, and the double pointed needle 152 into the container 80′. The fluid passage continues from the container 80′, through the double pointed needle 154 and the tube 144, into the auxiliary chamber 140.

Mixing is accomplished by first compressing the primary chamber 138 to urge liquid therein into the container 80′ and from the container into the auxiliary chamber 140. Next, the auxiliary chamber 140 is compressed, reversing the fluid flow, through the container 80′ to the primary chamber 138. This cycle is repeated until the first and second components 74′, 82′ are mixed. The port 100′ may then be opened and the mixture delivered. The use of the primary and auxiliary chambers 138, 140 and the container 80′ to establish a flow pattern is as disclosed in the U.S. patent application of Kaufman, et al., entitled "Container For Mixing a Liquid and a Solid", U.S. patent application Ser. No. 366,023 filed concurrently herewith and assigned to the assignee of the present invention.

The above-described closed device 136 provides a sterile pathway utilizing the sterile coupling, without the J-shaped configuration chamber.

Figure 13:
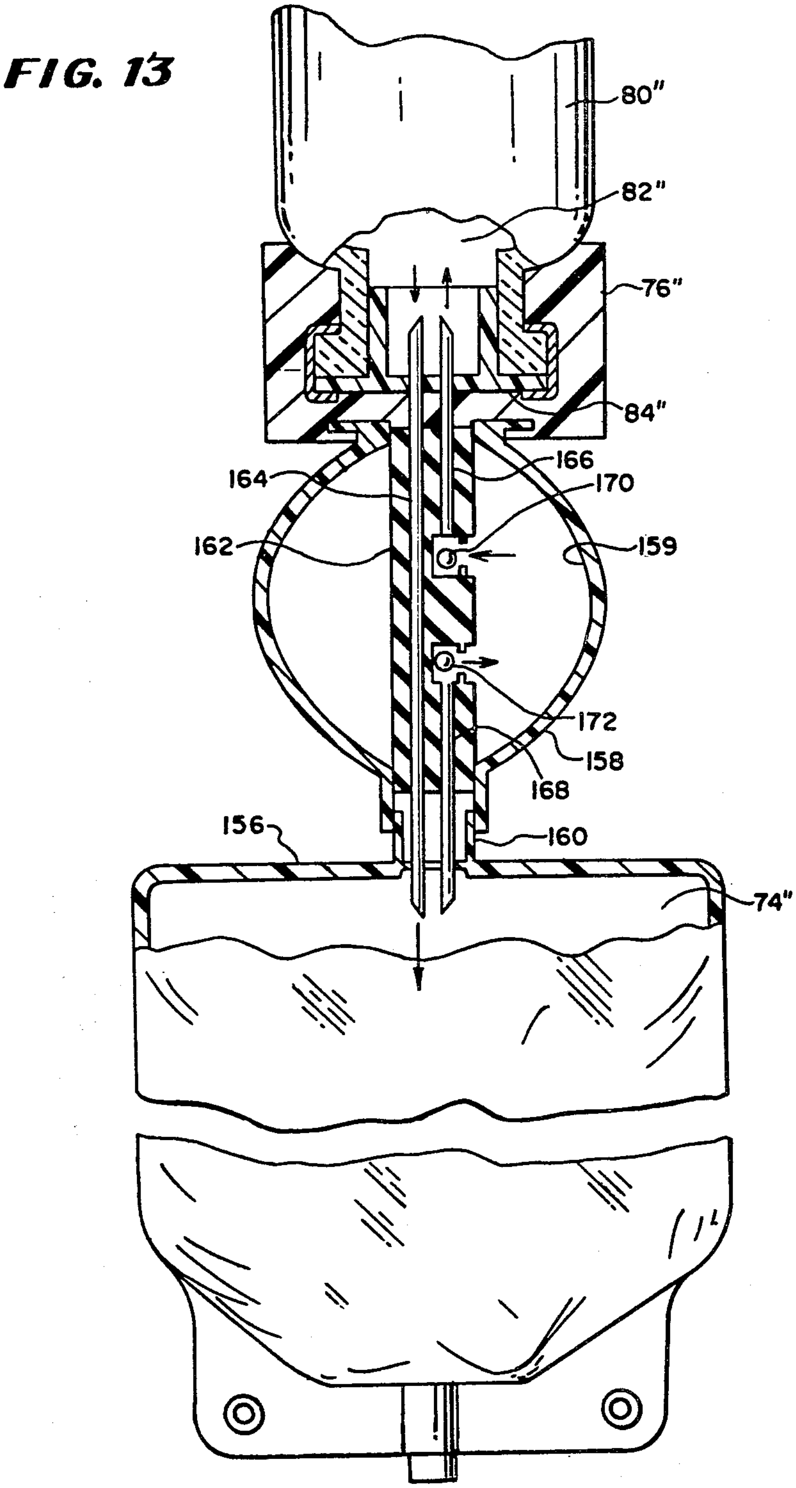
FIG. 13 illustrates an alternate embodiment of the sterile coupling.

Yet another embodiment of the sterile coupling is seen in FIG. 13. Here, the junction 76″ is affixed about a rubber stopper 84″ serving as an access means to a container 80″ or other receptacle. The junction 76″ connects the container 80″ to another receptacle, a first component storage unit 156. The access means to the storage unit 156 includes a flexible balloon 158 attached at one end to an inlet port 160 of the storage unit and at the other end to the junction 76″. The storgage unit access means further includes a needle housing 162 having a double pointed needle 164 and two single pointed needles 166, 168 mounted therein. The needle housing 162 further includes check valves 170, 172 providing one-way fluid communication between the balloon interior 159 and the single pointed needles 166, 168, respectively. The junction 76″ provides a sterile coupling between the rubber stopper 84″ and the storage unit access means.

Communication between the storage unit 156 and container 80″ is established by bringing the two receptacles toward each other, thereby compressing the balloon 158 as illustrated, forcing the needle housing 162 toward both the junction 76″ and the inlet port 160. The needles 164, 166 puncture the rubber stopper 84″. The needles 164, 168 puncture the inlet port 160. Fluid may then be transferred from the storage unit 156 through the single pointed needle 168 and into the balloon interior 159 through the check valve 172. The fluid may continue from the balloon interior 159 through the check valve 170 and the needle 166 into the container 80″. Fluid is free to flow from the container 80″ into the storage unit 156 through the double pointed needle 164. The balloon 158 and the check valve 170, 172 provide for mixture of the first and second components 74″ and 82″ within the balloon 158. The balloon 158 may be repeatedly squeezed to effect a pumping action, thereby mixing the first and second components 74″ and 82″.

While several embodiments and features have been described in detail herein and shown in the accompanying drawings, it will be evident that various further modifications are possible without departing from the scope of the invention.

What is claimed is:

1. A method for establishing and maintaining a sterile relation between the access means of each of two separate receptacles, each access means having an end portion, wherein at least one of the access means includes a piercing element, to provide for the selective establishment of a sterile pathway between the two receptacles, the steps comprising:

(a) maintaining the end portions in predetermined, spaced relation;
(b) injection molding molten material about at least the end portions of both access means;
(c) simultaneously sterilizing the end portions of both access means by heat transfer from the injection molded molten material; and
(d) cooling the molten material into a unitary junction means enclosing the end portions, the junction means maintaining the end portions in sterile relation, wherein the piercing element may be urged through the junction means so as to selectively establish a sterile pathway between the receptacles through both access means.

2. A method for establishing and maintaining a sterile relation between the access means of each of two separate receptacles, each access means having an end portion, wherein at least one of the access means includes a piercing element, to provide for the selective establishment of a sterile pathway between the receptacles, the steps comprising:

(a) biasing the end portions of the access means into abutting relation;
(b) injection molding molten material about at least the end portions of both access means, said injection molding step overcoming said bias and separating the end portions into spaced relation;
(c) simultaneously sterilizing the end portions of both access means by heat transfer from the injection molded molten material; and
(d) cooling the molten material into a unitary junction means enclosing the end portions, the junction means maintaining the end portions in sterile relation, wherein the piercing element may be urged through the junction means so as to selectively establish a sterile pathway between the receptacles through both access means.

3. A method for selectively establishing a sterile pathway between the access means of each of two separate receptacles, each access means having an end portion, wherein one of the access means includes a piercing element, the steps comprising:

(a) maintaining the end portions in predetermined, spaced relation;
(b) injection molding material about at least the end portions of both access means;
(c) simultaneously sterilizing the end portions of both access means by heat transfer from the injection molded molten material;
(d) cooling the molten material into a unitary junction means enclosing the end portions, the junction means maintaining the end portions in sterile relation; and
(e) selectively urging the piercing element through the junction means and the other of the access means thereby establishing a sterile pathway through both access means.

4. A method for selectively establishing a sterile pathway between access means of each of two separate receptacles, each access means having an end portion, wherein one of the access means includes a piercing element, the steps comprising:

(a) biasing the end portions of the access means into abutting relation;
(b) injection molding molten material about at least the end portions of both access means, said injection molding step overcoming said bias and separating the end portions into spaced relation;
(c) simultaneously sterilizing the end portions of both access means by heat transfer from the injection molded molten material;
(d) cooling the molten material into a unitary junction means enclosing the end portions, the junction means maintaining the end portions in sterile relation; and
(e) selectively urging the piercing element through the junction means and other of the access means, thereby establishing a sterile pathway through both access means.

* * * * *